US012586678B2

(12) United States Patent
Sugaya et al.

(10) Patent No.: US 12,586,678 B2
(45) Date of Patent: Mar. 24, 2026

(54) INSTRUMENT MANAGEMENT DEVICE FOR MEDICAL INSTRUMENT, INSTRUMENT MANAGEMENT SYSTEM, AND INSTRUMENT MANAGEMENT METHOD FOR MEDICAL INSTRUMENT

(71) Applicant: DGSHAPE Corporation, Hamamatsu (JP)

(72) Inventors: Akinori Sugaya, Hamamatsu (JP); Masaki Hanajima, Hamamatsu (JP); Akira Otaka, Hamamatsu (JP); Takaaki Kokubo, Hamamatsu (JP)

(73) Assignee: DGSHAPE Corporation, Shizuoka (JP)

( * ) Notice: Subject to any disclaimer, the term of this patent is extended or adjusted under 35 U.S.C. 154(b) by 1127 days.

(21) Appl. No.: 17/558,670

(22) Filed: Dec. 22, 2021

(65) Prior Publication Data

US 2022/0199243 A1      Jun. 23, 2022

(30) Foreign Application Priority Data

Dec. 23, 2020    (JP) ................................. 2020-214044

(51) Int. Cl.
*G16H 40/40*          (2018.01)
*A61L 2/26*           (2006.01)
(52) U.S. Cl.
CPC ............... *G16H 40/40* (2018.01); *A61L 2/26* (2013.01); *A61L 2202/17* (2013.01); *A61L 2202/24* (2013.01)

(58) Field of Classification Search
None
See application file for complete search history.

(56) References Cited

U.S. PATENT DOCUMENTS 7,050,867 B2 *   5/2006   Maymudes ........ G05B 19/4097
                                                        455/352
2003/0170901 A1 *  9/2003   Kippenhan ............... A61L 2/24
                                                         435/31

(Continued)

FOREIGN PATENT DOCUMENTS

JP          2006338047 A       12/2006
JP          2011036683 A        2/2011

(Continued)

*Primary Examiner* — Fateh M Obaid
(74) *Attorney, Agent, or Firm* — Keating & Bennett, LLP

(57)              ABSTRACT

An instrument management device includes a memory and a processor to execute a program stored in the memory to perform display processing, acquisition processing, and counting processing. In the display processing, in reissuing a sterilization label that is issued when sterilization processing is performed on an instrument set including medical instruments, a reissuance reason registration screen including a reason specifying area via which an operator specifies a type of reissuance reason is displayed on a display device. In the acquisition processing, the type of reissuance reason specified in the reason specifying area is acquired and stored in the memory. In the counting processing, for each type of reissuance reason stored in the memory, a number of times the sterilization label has been reissued for a reason of the type of reissuance reason is counted.

13 Claims, 9 Drawing Sheets

(56)     References Cited

U.S. PATENT DOCUMENTS

| | | | |
|---|---|---|---|
| 2006/0089118 A1* | 4/2006 | Whitehouse | H04B 1/202 |
| | | | 455/352 |
| 2018/0233030 A1* | 8/2018 | Knapp | H04L 12/2838 |
| 2018/0322445 A1* | 11/2018 | Sayles | G16H 40/20 |
| 2019/0051408 A1* | 2/2019 | Hanajima | G06Q 10/10 |
| 2019/0174208 A1* | 6/2019 | Speicher | G06F 1/163 |
| 2020/0061230 A1* | 2/2020 | Hammadi | A61L 9/16 |
| 2020/0258094 A1* | 8/2020 | Abrams | G06Q 30/018 |
| 2022/0085617 A1* | 3/2022 | Elisch | H02J 7/0044 |
| 2022/0160917 A1* | 5/2022 | Okuno | G06Q 10/06398 |

FOREIGN PATENT DOCUMENTS

| | | |
|---|---|---|
| JP | 2017-148113 A | 8/2017 |
| JP | 2020137702 A | 9/2020 |

* cited by examiner

TB30

130

| STERILIZATION ID | SET ID | SET NAME | RACK NAME | USER ID | USER NAME | REISSUANCE REASON | LABEL ISSUANCE DATE |
|---|---|---|---|---|---|---|---|
| 131 | 132 | 133 | 134 | 135 | 136 | 137 | 138 |
| 0000724 | 0000000247 | ⋮ | F[8] | 1 | DGS | – | ⋮ |
| 0000725 | 0000000249 | ⋮ | F[8] | 1 | DGS | EXPIRATION OF VALIDITY OF STERILIZATION | ⋮ |
| 0000726 | 0000000185 | ⋮ | F[8] | 1 | DGS | PACKAGE DAMAGE | ⋮ |
| 0000727 | 0000000247 | ⋮ | F[8] | 1 | DGS | LABEL DAMAGE | ⋮ |
| 0000728 | 0000000163 | ⋮ | F[8] | 1 | DGS | – | ⋮ |
| 0000729 | 0000000096 | ⋮ | F[8] | 1 | DGS | IC MISSING | ⋮ |
| ⋮ | ⋮ | ⋮ | ⋮ | ⋮ | ⋮ | ⋮ | ⋮ |

INSTRUMENT MANAGEMENT DEVICE FOR MEDICAL INSTRUMENT, INSTRUMENT MANAGEMENT SYSTEM, AND INSTRUMENT MANAGEMENT METHOD FOR MEDICAL INSTRUMENT

CROSS REFERENCE TO RELATED APPLICATIONS

This application claims the benefit of priority to Japanese Patent Application No. 2020-214044, filed on Dec. 23, 2020. The entire contents of this application are incorporated herein by reference.

BACKGROUND OF THE INVENTION

1. Field of the Invention

The present invention relates to an instrument management device for a medical instrument, an instrument management system, and an instrument management method for a medical instrument.

2. Description of the Related Art

For example, Japanese Laid-open Patent Publication No. 2017-148113 discloses a medical instrument repeatedly used in a medical practice, such as a surgical operation, a medical examination, or the like. The medical instrument can be repeatedly used by sequentially performing predetermined medical treatment processes. The medical treatment processes include a surgical operation process in which a surgical operation is performed, a collection process, a washing process, an assembling process, a sterilization process, and a storage process.

In the collection process, a medical instrument is collected after a surgical operation. In the washing process, the collected medical instrument is disassembled into a plurality of separated components and the components are washed. In the assembling process, the components of the medical instrument that have been washed are assembled. In the sterilization process, sterilization processing is performed on the medical instrument that has been assembled. In the storage process, the sterilized medical instrument is stored in a predetermined storage area. In the surgical operation process, the medical instrument stored in a storage area is dispensed and a surgical operation is performed using the dispensed medical instrument.

Incidentally, for example, each process of the above-described predetermined medical treatment processes is performed using an instrument set including one or more medical instruments as a unit. The one or more medical instruments forming the instrument set is housed, for example, in a predetermined packaging material, and sterilization processing in the sterilization process and storage in the storage process are performed thereon. When sterilization processing is performed on the instrument set in the sterilization process, a sterilization label in which a sterilization ID linked with the sterilization processing is recorded is issued. The sterilization label is attached to, for example, the packaging material in which the one or more medical instruments forming the instrument set are housed. Information of the instrument set on which sterilization processing has been performed and information of the sterilization processing are specified from the sterilization ID recorded in the sterilization label.

The sterilization label can be reissued. A possible reason for reissuance of the sterilization label is, for example, that the sterilization label or the packaging material to which the sterilization label is attached is damaged. It takes a considerable amount of time and effort of an operator in reissuing the sterilization label, and therefore, it is preferable that the number of times of reissuance of the sterilization label be reduced. Therefore, it is preferable to take countermeasures to reduce the number of times of reissuance of the sterilization label.

SUMMARY OF THE INVENTION

Preferred embodiments of the present invention provide instrument management devices for medical instruments and instrument management systems, and instrument management methods for medical instruments that each allow considering countermeasures for reducing the number of times of reissuance of a sterilization label.

An instrument management device for a medical instrument according to a preferred embodiment of the present invention includes a memory and at least one processor. The instrument management device is configured or programmed to execute display processing, acquisition processing, and counting processing. In the display processing, in reissuing a sterilization label that is issued when sterilization processing is performed on an instrument set including one or more medical instruments, a reissuance reason registration screen including a reason specifying area via which an operator specifies a type of reissuance reason that is a reason for reissuing the sterilization label is displayed on a display device. In the acquisition processing, the type of reissuance reason specified in the reason specifying area is acquired and is stored in the memory. In the counting processing, for each of the types of reissuance reason stored in the memory, the number of times of reissuance that is the number of times the sterilization label has been reissued for a reason of the type of reissuance reason is counted.

According to the instrument management device for a medical instrument according to a preferred embodiment of the present invention, in reissuing the sterilization label, the operator specifies the type of reissuance reason in the reason specifying area, so that for what reason the sterilization label is reissued can be stored in the memory. Then, for each of the types of reissuance reason, the number of times of reissuance is counted. Accordingly, the operator can know for what type of reissuance reason the sterilization label has been reissued many times by knowing the number of times of reissuance for each of the types of reissuance reason. Accordingly, the operator can consider countermeasures for reducing the number of times of reissuance for a reason of the type of reissuance reason for which the sterilization label has been reissued many times.

An instrument management method for a medical instrument according to a preferred embodiment of the present invention includes a display step, an acquisition step, and a counting step. In the display step, in reissuing a sterilization label that is issued when sterilization processing is performed on an instrument set including one or more medical instruments, a reissuance reason registration screen including a reason specifying area via which an operator specifies a type of reissuance reason that is a reason for reissuing the sterilization label is displayed on a display device. In the acquisition step, the type of reissuance reason specified in the reason specifying area is acquired and is stored in the memory. In the counting step, for each of the types of reissuance reason stored in the memory, the number of times of reissuance that is the number of times the sterilization label has been reissued for a reason of the type of reissuance reason is counted.

The above and other elements, features, steps, characteristics and advantages of the present invention will become more apparent from the following detailed description of the preferred embodiments with reference to the attached drawings.

DETAILED DESCRIPTION OF THE PREFERRED EMBODIMENTS

With reference to the attached drawings, instrument management devices for medical instruments (each of which will be hereinafter simply referred to as an instrument management device) according to preferred embodiments of the present invention will be described below. Note that, as a matter of course, preferred embodiments described herein are not intended to be particularly limiting the present invention.

Figure 1:
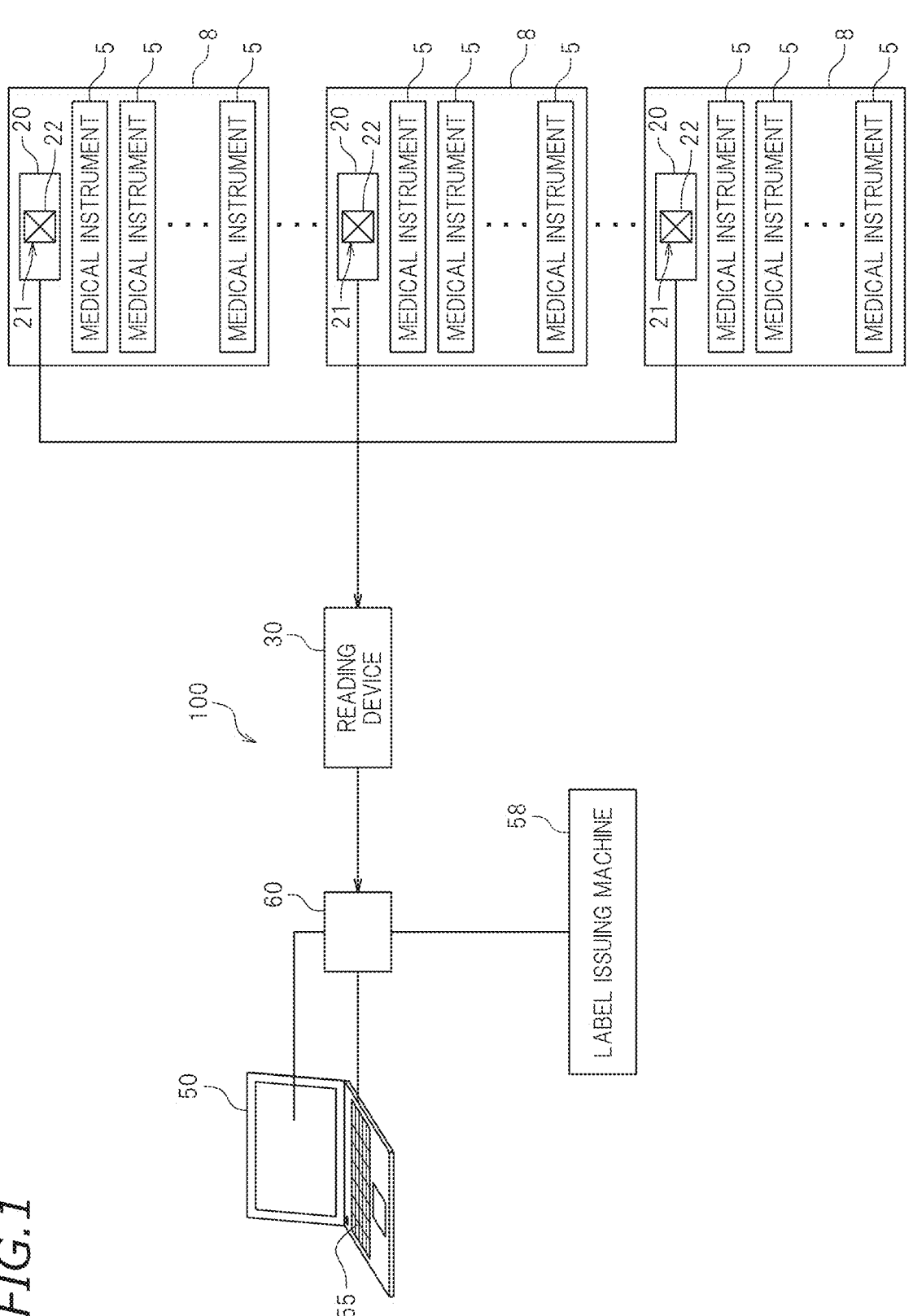
FIG. 1 is a schematic view illustrating an instrument management system according to a preferred embodiment of the present invention.

FIG. 1 is a schematic view illustrating an instrument management system 100 according to this preferred embodiment. The instrument management system 100 is used in managing a medical instrument 5 that is repeatedly used.

The medical instrument 5 is an instrument that is used in a medical practice that is performed in a medical site, such as a hospital or the like. The medical practice is a practice related to a medical activity that is performed for a patient by a doctor. Examples of a medical practice include a surgical operation and a medical examination.

The medical instrument 5 is, for example, a trocar, forceps, an incision device, a washing and sucking device, scissors, a scalpel (for example, a laser scalpel or an electric scalpel), an ultrasonic cutter, a scalpel holder, a cannula, tweezers, a retractor, a scale, a sonde, an elevator, a rasp, a suction tube, a rib retractor, a rib contractor, a needle holder, an injector, a metal ball, a pus tray, a cup, a pin, a mirror, a file, an opening tool, a clamp, a handpiece, an elevatorium, a chisel, a sharp spoon, a raspatory, a speculum, a suture needle, a punch, a water receiver, a needle, a penetrator, a bougie, a vent pipe, a bone impactor, a luer, a radio plier, a hammer, an angle gauge, a thermometer, a perforator, a spuit, a metal swab, an enema, a syringe, an endoscope, or the like. However, the above-described examples are merely some examples of the medical instrument 5. The medical instrument 5 is not limited to the above-described examples.

The medical instrument 5 may be formed of a single part and may be formed of a plurality of parts. Examples of the medical instrument 5 formed of a plurality of parts include, for example, a trocar, forceps, an incision device, a washing and sucking device, or the like which is used in a laparoscopic surgical operation. The medical instrument 5 described above is formed of a plurality of components, is collected, for example, after a surgical operation, and is disassembled into a plurality of separated components. Parts that form the medical instrument 5 are referred to as components herein. Also, in some cases, such a component is further formed of a plurality of components, and in such a case, all of the components are referred to as components.

Figure 2:
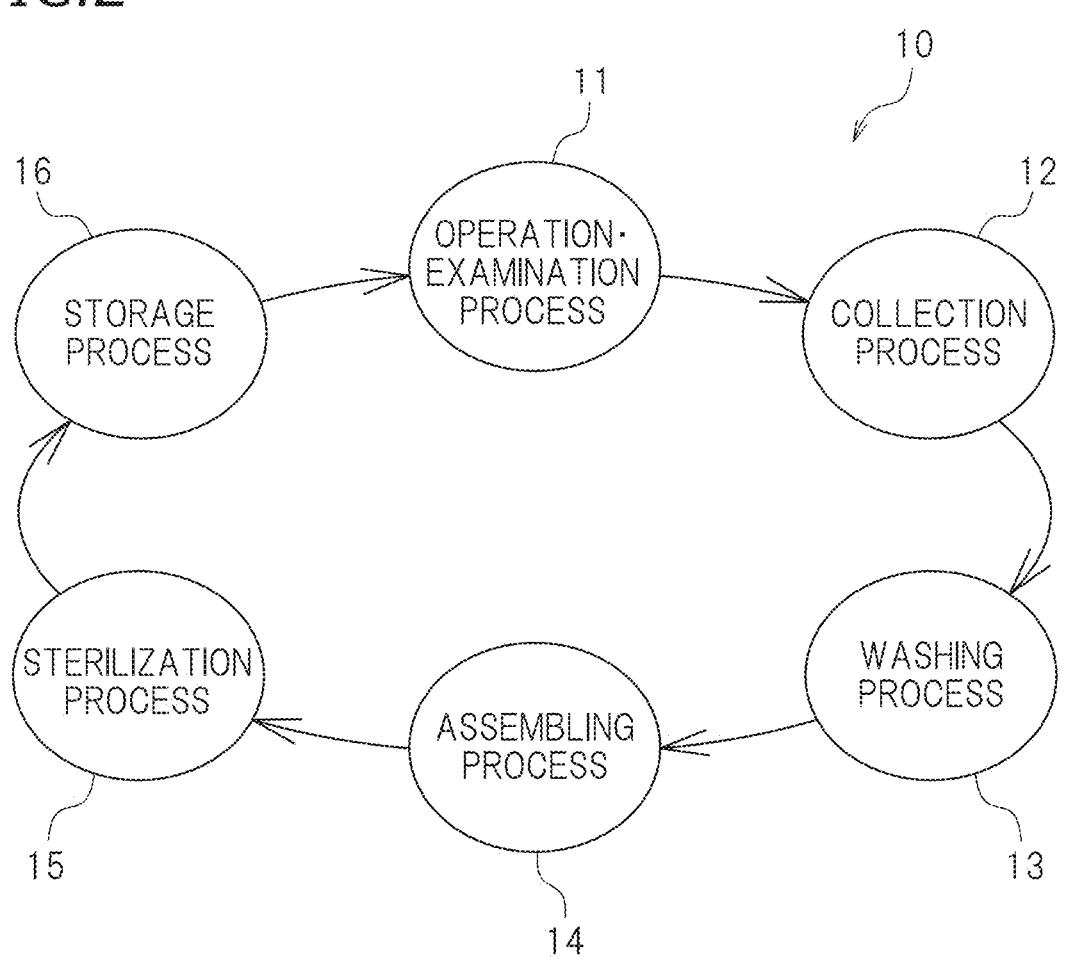
FIG. 2 is a diagram illustrating a circulation cycle.

FIG. 2 is an explanatory diagram of a circulation cycle 10. As illustrated in FIG. 2, the medical instrument 5 is repeatedly usable in a predetermined circulation cycle 10. Note that the number of repetitions of use of one medical instrument 5 in the circulation cycle 10 is not particularly limited and is determined in accordance with a type of the medical instrument 5 or a component of the medical instrument 5, as appropriate. In this preferred embodiment, the circulation cycle 10 includes an operation and examination process 11, a collection process 12, a washing process 13, an assembling process 14, a sterilization process 15, and a storage process 16.

The operation and examination process 11 is a process in which a surgical operation or a medical examination which is an example of a medical practice is performed using the medical instrument 5. In the operation and examination process 11, the medical instrument 5 that is stored in a predetermined storage area is dispensed (in other words, is taken out) and a surgical operation or a medical examination is performed using the dispensed medical instrument 5.

The collection process 12 is a process that is performed after the operation and examination process 11. The collection process 12 is a process in which the medical instrument 5 that has been used in a surgical operation or a medical examination is collected. Note that, in a case where the medical instrument 5 is formed of a plurality of components, the collection process 12 may include an operation of disassembling the medical instrument 5 into individual components.

The washing process 13 is a process that is performed after the collection process 12. The washing process 13 is a process in which the medical instrument 5 or each of the individual components of the medical instrument 5 that has been collected in the collection process 12 is washed. In the washing process 13, for example, using a washer (not illustrated), washing of the medical instrument 5 is performed.

The assembling process 14 is a process that is performed after the washing process 13. The assembling process 14 is a process in which the components of the medical instrument 5 which have been washed in the washing process 13 are assembled to complete the single medical instrument 5. The assembling process 14 is a process in which the medical instrument 5 that is formed of a plurality of components is assembled. For example, for the medical instrument 5 that is formed of a single component or the medical instrument 5 that has not been disassembled in the collection process 12, the assembling process 14 may be omitted.

The sterilization process 15 is a process that is performed after the assembling process 14. The sterilization process 15 is a process in which the medical instrument 5 that has been assembled in the assembling process 14 is sterilized. In the sterilization process 15, for example, using a sterilizer (not illustrated), sterilization processing of the medical instrument 5 is performed. Sterilization processing will be hereinafter also referred to as merely as sterilization.

The storage process 16 is a process that is performed after the sterilization process 15. The storage process 16 is a process in which the medical instrument 5 on which sterilization processing has been performed is stored in the predetermined storage area. Note that, after the storage process 16, the operation and examination process 11 is performed.

In the circulation cycle 10 according to this preferred embodiment, each process is performed using an instrument set 8 illustrated in FIG. 1 as a unit. The instrument set 8 is a set including one or more medical instruments 5. There is no particular limitation on a method for dividing the plurality of medical instruments 5 into one or more instrument sets 8. The number and types of the medical instruments 5 included in the instrument set 8 are determined for each medical site, such as a hospital or the like and, in some cases, are determined based on empirical rules of staff members, such as a doctor, a nurse, an operator of each process of the circulation cycle 10, or the like.

For example, the instrument set 8 is a set including one or more medical instruments 5 that are used in one medical practice (for example, a surgical operation or a medical examination). The number of instrument sets 8 used in one surgical operation or one medical examination may be one and may be plural.

Incidentally, in this preferred embodiment, after each of the one or more medical instruments 5 is assembled in the assembling process 14 in FIG. 2, the one or more medical instruments 5 are put together in units of the instrument set 8. Herein, the one or more medical instruments 5 included in one instrument set 8 is housed in a predetermined packaging body 6 illustrated in FIG. 3. Housing the one or more medical instrument 5 included in the instrument set 8 in the packaging body 6 will be hereinafter referred to as housing the instrument set 8 in the packaging body 6. Herein, in a state where the instrument set 8 is housed in the packaging body 6, the packaging body 6 is sealed. In a state where the instrument set 8 is housed in the packaging body 6, the instrument set 8 is sterilized in the sterilization process 15 and is stored in the storage process 16.

Note that, in this preferred embodiment, there is no particular limitation on a type of the packaging body 6, and the packaging body 6 may be a packaging body that can wrap or pack the one or more medical instruments 5 included in the instrument set 8. Herein, as the packaging body 6, a sealed pouch-shaped package illustrated in FIG. 3 may be used, but the packaging body 6 is not limited thereto. For example, as the packaging body 6, a container that houses the instrument set 8 may be used. There is no particular limitation on a material of the packaging body 6. For example, the packaging body 6 may be formed of a nonwoven fabric. For example, the packaging body 6 may be formed of aluminum or paper, and may be formed of a synthetic resin, such as polyethylene, polypropylene, or the like.

Figure 3:
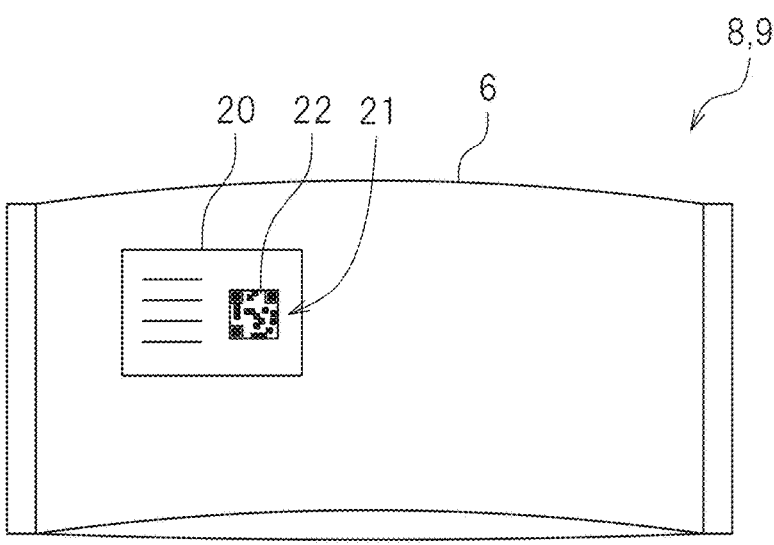
FIG. 3 is a view illustrating an example of an instrument set.

In this preferred embodiment, when sterilization processing is performed on the instrument set 8 in the sterilization process 15, a sterilization label 20 illustrated in FIG. 3 is issued. The sterilization label 20 is attached to, for example, the packaging body 6 in which the instrument set 8 is housed. A sterilization identification mark 21 is assigned to the sterilization label 20. As illustrated in FIG. 1, the sterilization identification mark 21 is read by a reading device 30 that will be described later. There is no particular limitation on a type of the sterilization identification mark 21. For example, the sterilization identification mark 21 may be a one-dimensional code, may be a two-dimensional code, and may be an IC tag. In this preferred embodiment, as illustrated in FIG. 3, the sterilization identification mark 21 is a two-dimensional code.

For example, a target sterilization ID 22 is recorded in the sterilization identification mark 21. The target sterilization ID 22 is an ID assigned to the instrument set 8 on which sterilization processing is performed or sterilization processing has been performed when the sterilization label 20 is issued. The target sterilization ID 22 is a specific ID that is assigned to the instrument set 8 each time the sterilization label 20 is issued.

Note that other information than the sterilization identification mark 21, that is, for example, information related to sterilization processing (for example, a sterilization type, a term of validity of sterilization processing, or the like) or information related to the instrument set 8 (for example, a set name of the instrument set 8, a rack name of a rack in which the instrument set 8 is stored, or the like), may be assigned to the sterilization label 20.

In this preferred embodiment, issuing the sterilization label 20 includes printing the two-dimensional coded sterilization identification mark 21 in which the target sterilization ID 22 is recorded and the above-described information of sterilization processing and the instrument set 8 on a predetermined label medium (for example, label paper) to produce the sterilization label 20.

Incidentally, the sterilization label 20 can be reissued. For example, in reissuing the sterilization label 20, the sterilization identification mark 21 or the like is printed on the label medium and the sterilization label 20 is produced again. An operator attaches the produced sterilization label 20 to the packaging body 6 again. Thus, it takes time and efforts of the operator to reissue the sterilization label 20, and therefore, it is preferable that the number of times of reissuance of the sterilization label 20 is reduced. Therefore, it is preferable to take countermeasures to reduce the number of times of reissuance of the sterilization label 20.

However, conventionally, how often the sterilization label 20 is reissued has not been recognized and a reason why the sterilization label 20 is reissued has not been acknowledged. Therefore, it has been difficult to consider countermeasures to reduce the number of times of reissuance of the sterilization label (which will be hereinafter referred to as the number of times of reissuance).

Thus, in this preferred embodiment, in the instrument management system 100 illustrated in FIG. 1, the number of times of reissuance of the sterilization label 20 is tabulated for each of types of reasons for reissuance of the sterilization label 20 (which will be hereinafter referred to as reissuance reasons). Then, the operator recognizes, based on information obtained by tabulating the number of times of reissuance of the sterilization label 20, for what type of reissuance reason the number of times of reissuance is large. The operator considers countermeasures for reducing reissuances of the sterilization label 20 for a type of reissuance reason for which reissuance has frequently occurred.

Note that, in this preferred embodiment, reissuing the sterilization label 20 includes issuing the sterilization label 20 again before the instrument set 8 is used in the operation and examination process 11. Note that, when the sterilization label is reissued, information that has been assigned to the sterilization label 20 and is related to sterilization processing (for example, a sterilization type or the like, excluding a term of validity of sterilization processing) and information related to the instrument set 8 (for example, a set name of the instrument set 8, a rack name of a rack in which the instrument set 8 is stored, or the like) are not basically changed.

In this preferred embodiment, as illustrated in FIG. 1, the instrument management system 100 includes a reading device 30, a display device 50, an operation device 55, a label issuing machine 58, and an instrument management device 60.

The reading device 30 is operated by the operator and reads the target sterilization ID 22 by reading the sterilization identification mark 21 of the sterilization label 20 assigned to the instrument set 8. Although not illustrated, the reading device 30 is provided with a handle that is gripped by the operator's hand.

Note that there is no particular limitation on a type of the reading device 30, and the reading device 30 may be a device that can read the target sterilization ID 22 of the sterilization identification mark 21. For example, in a case where the sterilization identification mark 21 is a two-dimensional code, the reading device 30 may be a two-dimensional code reader that can read a two-dimensional code. For example, in a case where the sterilization identification mark 21 is an IC tag, the reading device 30 may be an IC tag reader. In this preferred embodiment, the reading device 30 is a non-contact type device. However, the reading device 30 may be a contact type device. Note that the number of the reading devices 30 may be one and may be plural.

A screen related to reissuance of the sterilization label 20 or the like is displayed on the display device 50. Note that there is no particular limitation on a type of the display device 50. For example, the display device 50 may be a display of a mobile terminal. The display device 50 may be a display of a desktop type or notebook type (in other words, laptop type) personal computer.

The operation device 55 is used when the operator operates a screen displayed on the display device 50 or the like. The screen displayed on the steering 50 can be switched, for example, by the operator's operation of the operation device 55. Moreover, a reissuance reason type of the sterilization label 20 can be input by the operator's operation of the operation device 55. Note that there is no particular limitation on a type of the operation device 55. For example, the operation device 55 is, for example, a keyboard, a mouse, or the like of the personal computer. However, the operation device 55 may be a touch panel provided on the display device 50. Note that each of the number of the display devices 50 and the number of the operation devices 55 is one herein, but may be plural.

The label issuing machine 58 issues the sterilization label 20. Herein, the label issuing machine 58 prints the sterilization identification mark 21 in which the target sterilization ID 22 is recorded on a predetermined label medium (for example, label paper) or the like. The sterilization label 20 is produced by printing the sterilization identification mark 21 or the like on the label medium. The label medium is, for example, a seal material. The seal material includes, for example, a base sheet and a printing sheet that is stuck to a surface of the base sheet via an adhesive member, such as an adhesive or the like. The sterilization identification mark 21 or the like is printed on the printing sheet, and the printing sheet is peeled from the base sheet and is used as the sterilization label 20. Note that there is no particular limitation on a type of the label issuing machine 58 but, in this preferred embodiment, the label issuing machine 58 is realized by a so-called printer.

Figure 4:
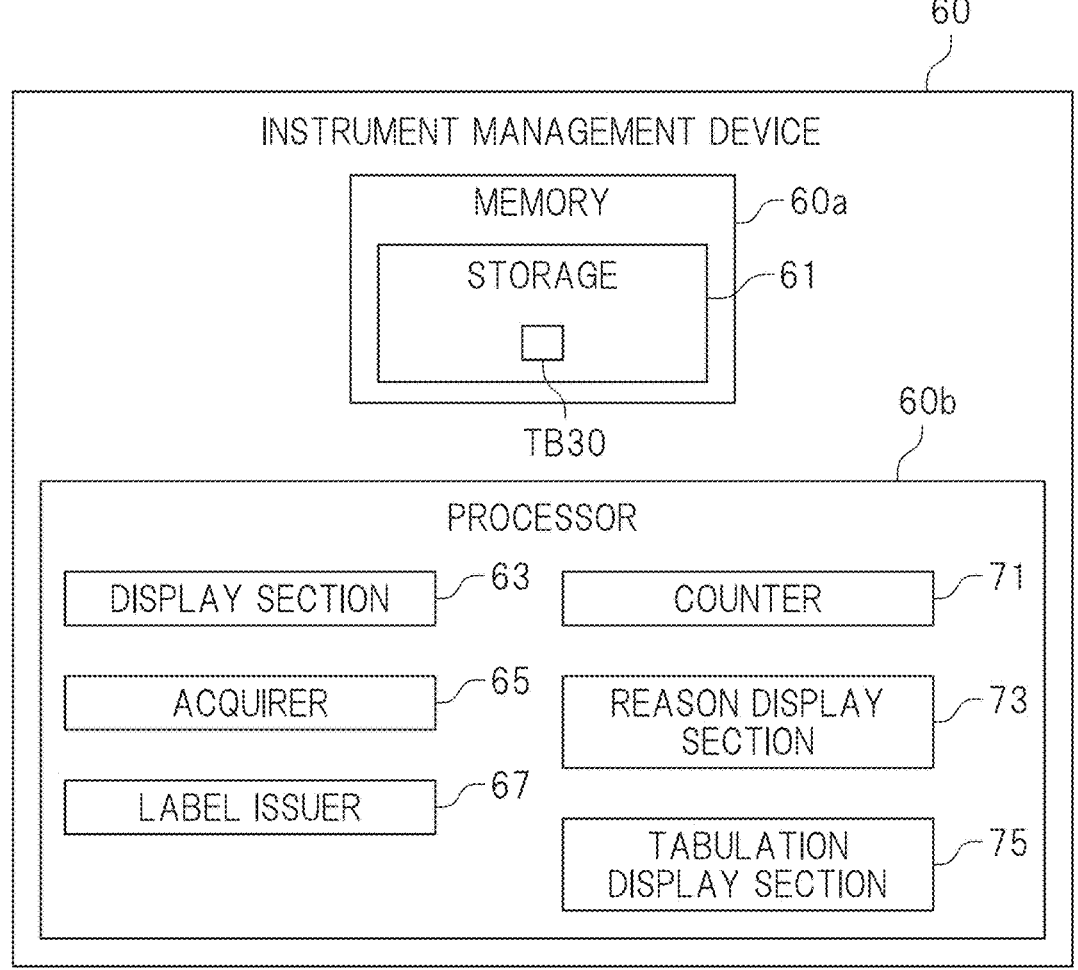
FIG. 4 is a block diagram of an instrument management device.

Next, the instrument management device 60 according to this preferred embodiment will be described. The instrument management device 60 is a device that instructs to issue the sterilization label 20 and records and tabulates types of reissuance reasons for the sterilization label 20. The instrument management device 60 is a computer control device. FIG. 4 is a block diagram of the instrument management device 60. As illustrated in FIG. 4, the instrument management device 60 includes a memory 60*a* and at least one processor 60*b*. The number of the processors 60*b* may be one and may be plural. For example, the processor 60*b* uses a program stored in the memory 60*a*, and thus, can execute processing. The instrument management device 60 may be realized by a dedicated computer and may be realized by a general-purpose computer.

In this preferred embodiment, as illustrated in FIG. 1, the instrument management device 60 is communicably connected to the reading device 30. The instrument management device 60 may be connected to the reading device 30 via a wired communication and may be connected thereto via a wireless communication. The instrument management device 60 is communicably connected to the display device 50 and the operation device 55. Note that the instrument management device 60, the display device 50, and the operation device 55 may be realized by one personal computer. In this preferred embodiment, the instrument management device 60 is communicably connected to the label issuing machine 58.

Herein, the instrument management system 100 may be realized by a so-called client-server system, and may be realized by a cloud computing. Moreover, the instrument management system 100 may be realized by a so-called stand-alone system.

In this preferred embodiment, as illustrated in FIG. 4, the instrument management device 60 includes a storage 61, a display section 63, an acquirer 65, a label issuer 67, a counter 71, a reason display section 73, and a tabulation display section 75. The storage 61 is stored in the memory 60*a*. The display section 63, the acquirer 65, the label issuer 67, the counter 71, the reason display section 73, and the tabulation display section 75 can be executed by the processor 60*b*.

Figure 5:
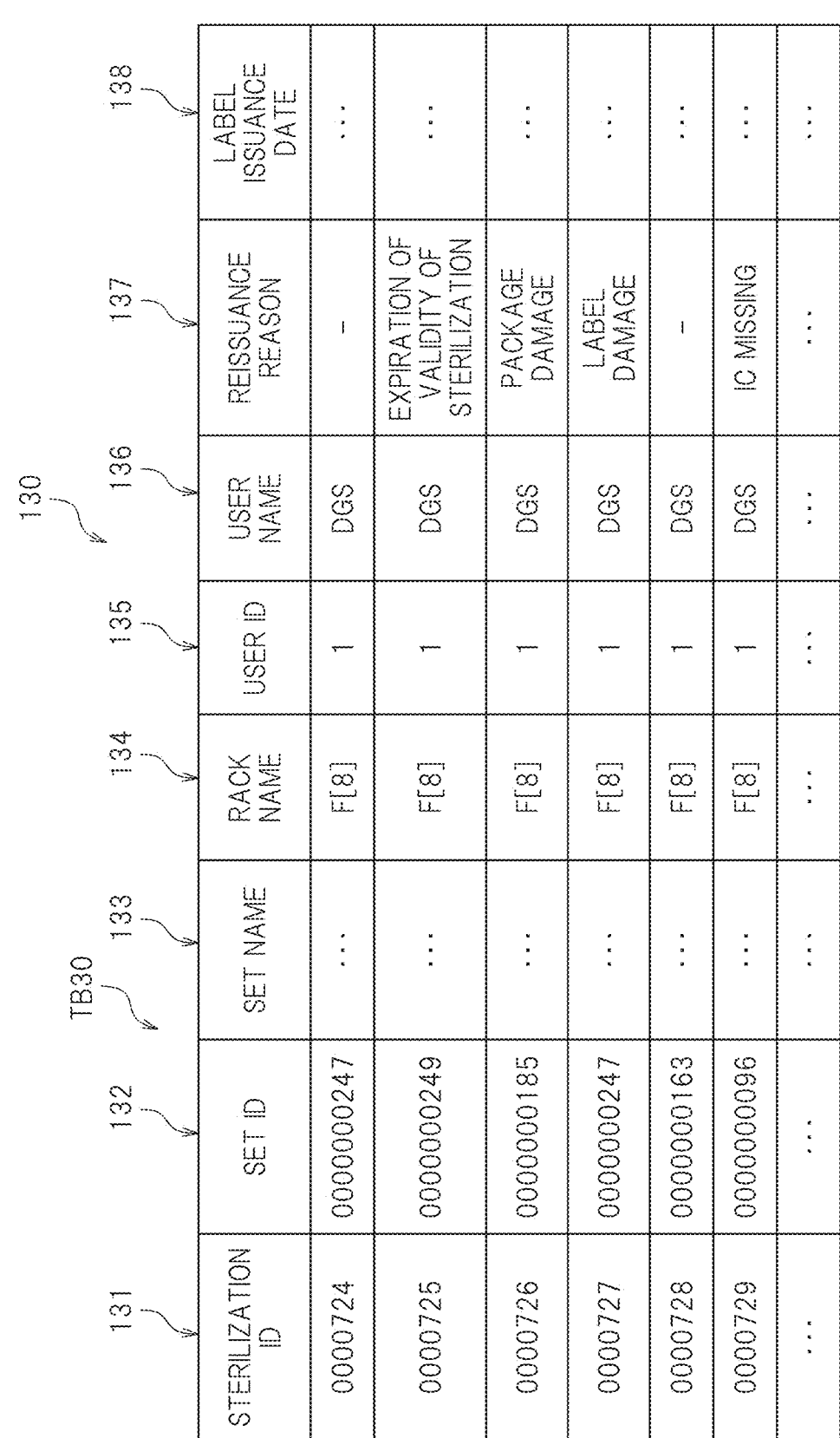
FIG. 5 is a table illustrating a configuration example of a sterilization label information table.

In this preferred embodiment, in the storage 61 realized by the memory 60*a*, a sterilization label information list table TB30 illustrated in FIG. 5 is stored in advance.

As illustrated in FIG. 5, the sterilization label information list table TB30 is a table in which sterilization label information 130 for the instrument set 8 is stored. The sterilization label information 130 is information generated in issuing the sterilization label 20, for example, whether the sterilization label 20 is reissued or is issued for the first time. The sterilization label information 130 is, for example, information in which a sterilization ID 131, a set ID 132, a set name 133, a rack name 134, a user ID 135, a user name 136, a reissuance reason type 137, and a label issuance date 138 are associated with one another. Herein, in the sterilization label information 130, there are at least items of the sterilization ID 131, the set ID 132, the set name 133, the rack name 134, the user ID 135, the user name 136, the reissuance reason type 137, the label issuance date 138, and the like.

As used herein, "associated with one another" represents a state where items are described in a same row of the table. "Associated with one another" can be paraphrased as "corresponding to one another" or "linked with one another."

The sterilization ID 131 of FIG. 5 is a specific ID that is automatically issued when the sterilization label 20 is issued. The sterilization ID 131 is an ID that is assigned to the instrument set 8 on which sterilization processing is performed. Herein, it is determined that the sterilization label 20 has been issued to the instrument set 8 assigned the sterilization ID 131. The set ID 132 is a specific set ID assigned to a target instrument set 8 to which the sterilization label 20 has been issued. The set name 133 is a set name of the target instrument set 8 to which the sterilization label 20 has been issued.

The rack name 134 is a name of a rack in which the target instrument set 8 to which the sterilization label 20 has been issued is stored. The user ID 135 is an ID of the operator who issued the sterilization label 20. The user name 136 is a name of the operator who issued the sterilization label 20. Herein, the user ID 135 and the user name 136 correspond to user information (not illustrated) stored in a user master table (not illustrated).

A reason for reissuing the sterilization label 20 is indicated in the reissuance reason type 137. Note that, in a case where the sterilization label 20 is not reissued but is issued for the first time, nothing is indicated in the reissuance reason type 137 and, for example, a null character is indicated. The label issuance date 138 is a date of issuance of the sterilization label 20.

Next, process steps of processing of the instrument management device 60 in reissuing the sterilization label 20 will be described with reference to a flowchart of FIG. 6.

Figure 6:
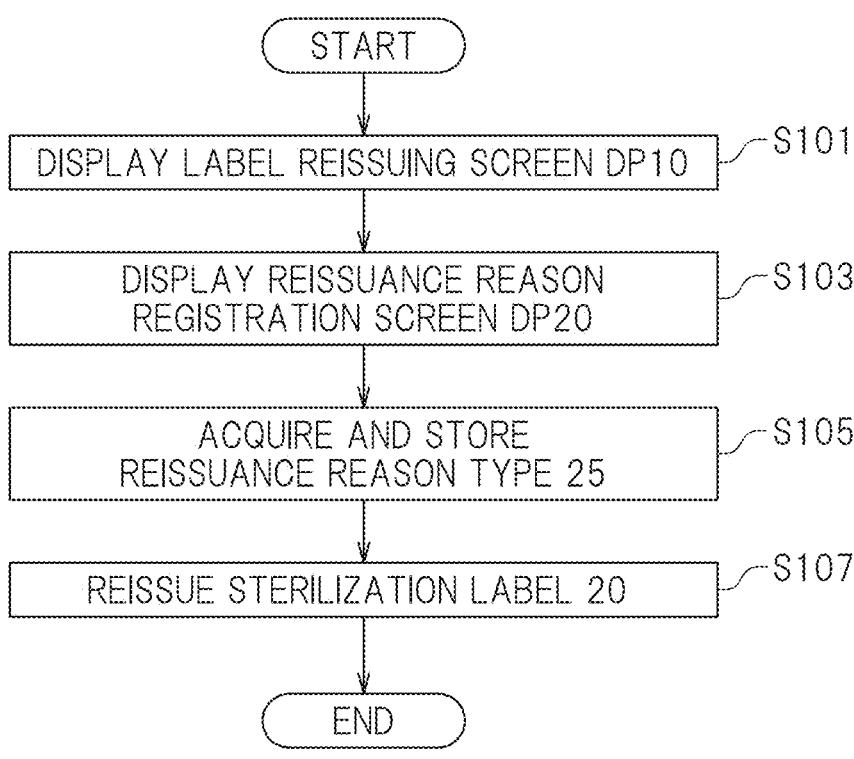
FIG. 6 is a flowchart illustrating process steps of processing of the instrument management device in reissuing the sterilization label.

In this preferred embodiment, when a necessity for reissuing the sterilization label 20 arises, in Step S101 of FIG. 6, the display section 63 of FIG. 4 displays a label reissuing screen DP10 (see FIG. 7) on the display device 50. Although not illustrated, for example, a screen on which a display button used for displaying the label reissuing screen DP10 is arranged is displayed on the display device 50. The operator presses (for example, clicks) the display button via the operation device 55, so that the display section 63 displays the label reissuing screen DP10 on the display device 50.

Note that there is no particular limitation on a configuration of the label reissuing screen DP10. In this preferred embodiment, a plurality of areas 101 to 107 on which information related to the instrument set 8 to which the sterilization label 20 is reissued or information related to sterilization processing is displayed are arranged on the label reissuing screen DP10. For example, on the label reissuing screen DP10, an image area 101 in which an image of the instrument set 8 is displayed, a parts number area 102 in which the number of the medical instruments 5 forming the instrument set 8 is displayed, a department area 103 in which a belonging department (clinical department) is displayed, a container area 104 in which a type of container in which the instrument set 8 is placed is displayed, a type area 105 in which a sterilization type when sterilization processing is performed is displayed, a rack name area 106 in which a rack name of a storage destination of the instrument set 8 is displayed, and a note area 107 in which notes, such as cautions or the like, for the instrument set 8 are displayed are arranged. In the note area 107, for example, in a case of the instrument set 8 to which the sterilization label 20 has been reissued in the past, a date of reissuance of the sterilization label 20 and a reissuance reason type are displayed.

Note that there is no particular limitation on a method for displaying information in each of the areas 101 to 107 of the label reissuing screen DP10. For example, each of the areas 101 to 107 may be configured by a text box, and information may be manually input in each of the areas 101 to 107 by the operator and may be automatically input therein. For example, in the storage 61 of FIG. 4, an instrument set information (not illustrated) in which a set ID of the instrument set 8, an image file name of an image of the instrument set 8, the number of the medical instruments 5 of the instrument set 8, a belonging department, a container type, a sterilization type, and a rack name are associated with one another is stored.

For example, a target set ID 9 (see FIG. 3) is assigned to the target instrument set 8 to which it is desired to reissue the sterilization label 20. Thus, the instrument management device 60 acquires the target set ID 9 of the target instrument set 8 to which the sterilization label 20 is reissued. Then, the instrument management device 60 extracts the instrument set information having the same set ID as the acquired target set ID 9 and the display section 63 displays, based on the extracted instrument set information, information related to the instrument set 8 assigned the target set ID 9, that is, information of the instrument set 8 that is a target to which the sterilization label 20 is reissued herein, in each of the areas 101 to 107 of the label reissuing screen DP10.

Note that there is no particular limitation on a method for acquiring the target set ID 9. For example, the sterilization identification mark 21 of the sterilization label 20 that has been issued to the target instrument set 8 before is read by the reading device 30 to acquire the target sterilization ID 22 (see FIG. 1). Next, the sterilization ID 131 that is the same as the target sterilization ID 22 may be extracted from the sterilization label information 130 to acquire the set ID 132 associated with the extracted sterilization ID 131 as the target set ID 9.

Figure 7:
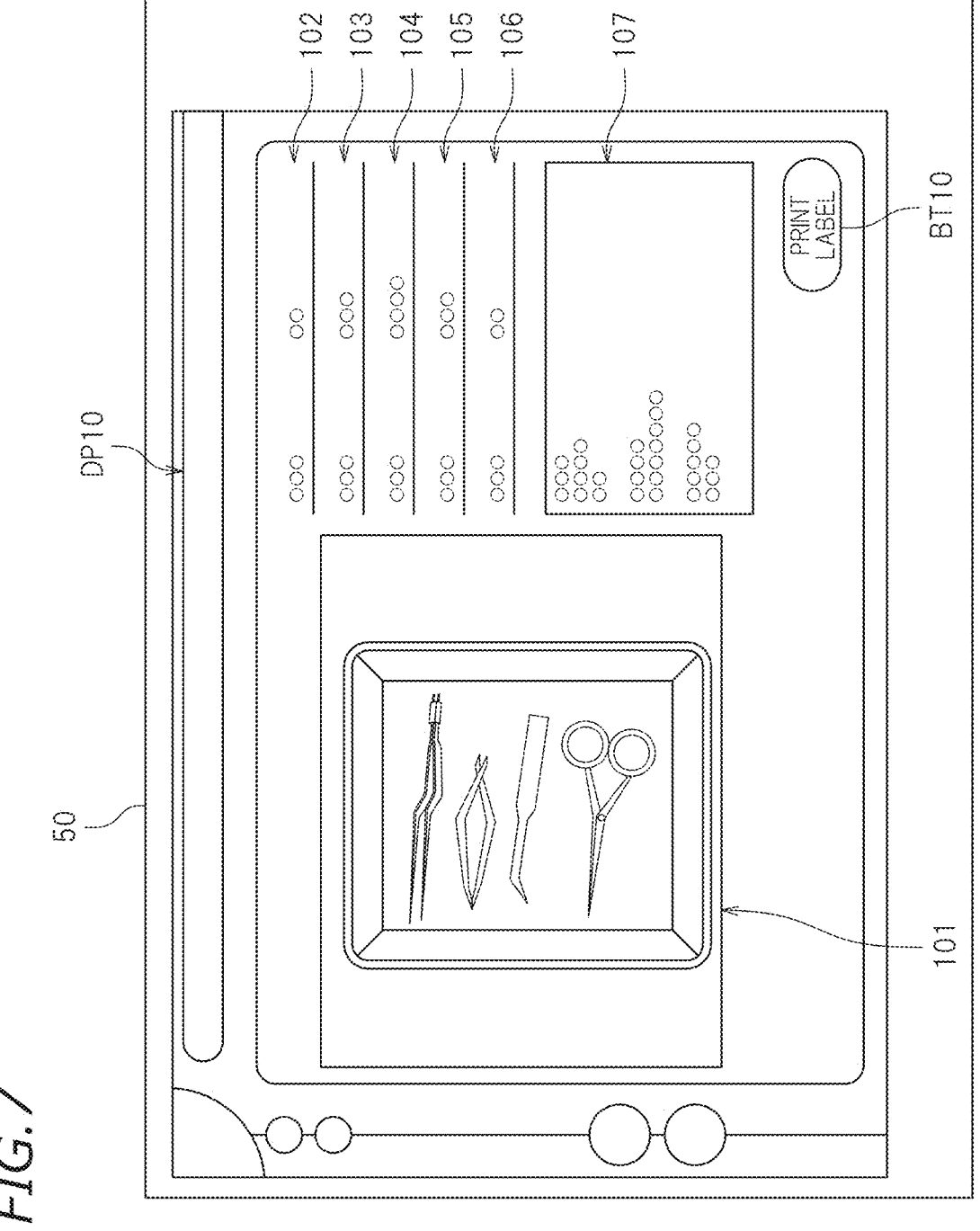
FIG. 7 is a view illustrating a label reissuance screen.

In this preferred embodiment, as illustrated in FIG. 7, a label issuing button BT10 is arranged on the label reissuing screen DP10. The operator presses the label issuing button BT10 via the operation device 55 and the process proceeds to Step S103 of FIG. 6 next.

Figure 8:
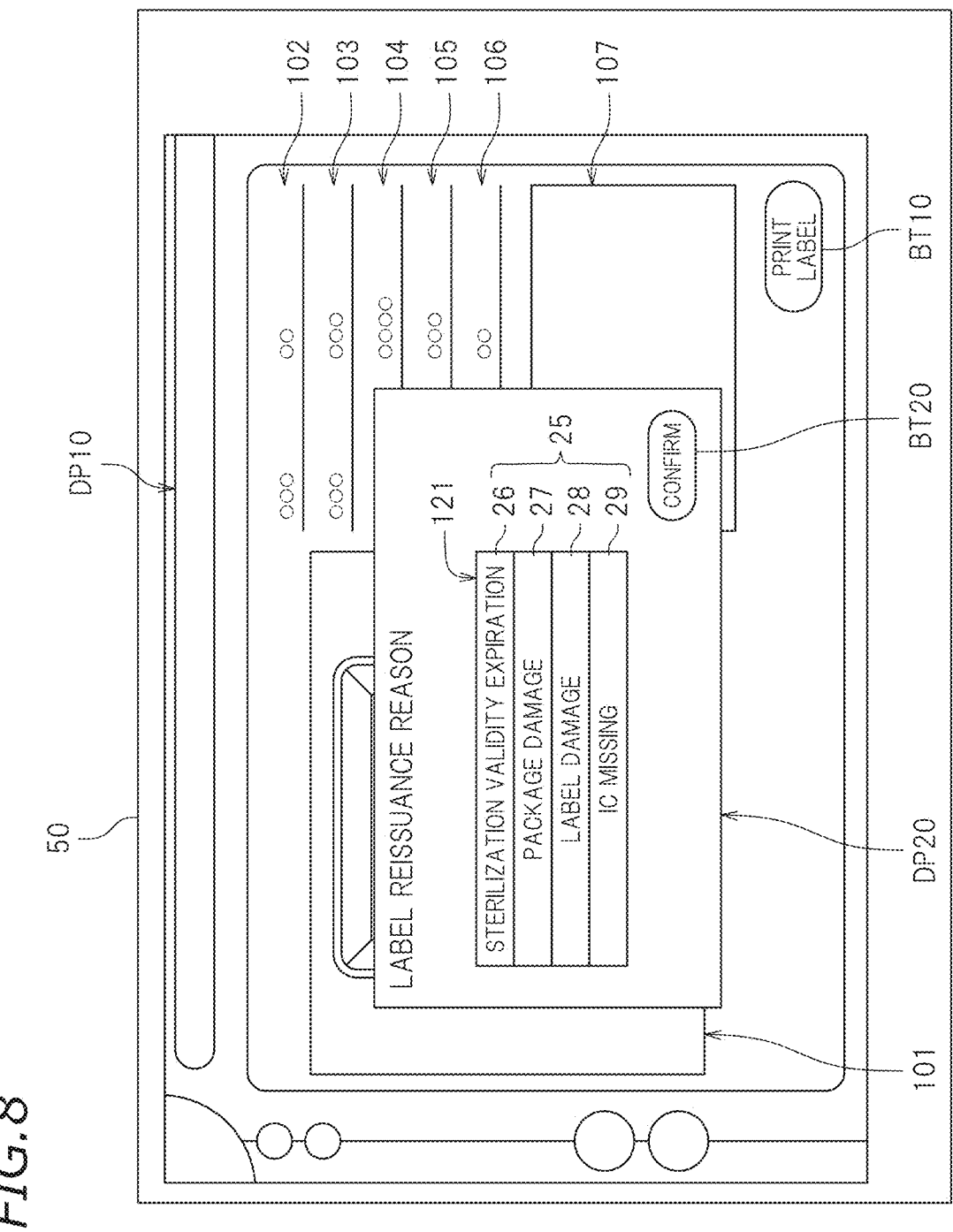
FIG. 8 is a view illustrating a reissuance reason registration screen.

In Step S103, the display section 63 of FIG. 4 displays a reissuance reason registration screen DP20 on the display device 50. As illustrated in FIG. 8, the reissuance reason registration screen DP20 is a screen used for registering a type of reissuance reason for the sterilization label 20 by the operator. Herein, a reason specifying area 121 used for specifying a reissuance reason and a confirmation button BT20 are arranged on the reissuance reason registration screen DP20.

The reason specifying area 121 is an area via which the operator specifies a reissuance reason type 25 of the sterilization label 20. In this preferred embodiment, the reason specifying area 121 is configured such that the operator selects the reissuance reason type 25 via the reason specifying area 121. However, for example, the reason specifying area 121 may be configured by a text box, and may be configured such that the operator manually inputs the reissuance reason type 25 in the reason specifying area 121 via the operation device 55.

Herein, the reason specifying area 121 is realized by a selection list via which the operator can select a reissuance reason. In this preferred embodiment, as the reissuance reason type 25 of the sterilization label 20, a sterilization validity expiration reason 26, a package damage reason 27, a label damage reason 28, an IC missing reason 29 are included. However, reasons included as the reissuance reason type 25 are not limited to the reasons 26 to 29. Some other reason may be included in the reissuance reason type 25.

Herein, the sterilization validity expiration reason 26 is a reason for reissuance of the sterilization label 20 set for a case where a term of validity of sterilization processing for the instrument set 8 has expired and sterilization processing is performed again. As in this case, when the term of validity of sterilization processing has expired, sterilization processing is performed on the instrument set 8 again under the same conditions for sterilization processing. The sterilization label 20 is reissued for sterilization processing that is performed again.

As for the package damage reason 27, it is set as a reason for reissuance of the sterilization label 20 that the packaging body 6 (see FIG. 3) housing the one or more medical instruments 5 forming the instrument set 8 is damaged. For example, when the packaging body 6 is damaged, the damaged packaging body 6 is discarded with the sterilization label 20 attached thereto. Therefore, the instrument set 8 is housed in a new packaging body 6 and the sterilization label 20 is reissued so as to be attached to the new packaging body 6.

As for the label damage reason 28, it is set as a reason for reissuance of the sterilization label 20 that the sterilization label 20 attached to the packaging body 6 housing the instrument set 8 is damaged. When the sterilization label 20 attached to the packaging body 6 is torn or is damaged in some other manner and the reading device 30 cannot read the sterilization identification mark 21 of the sterilization label 20, the sterilization label 20 is reissued.

As for the IC missing reason 29, it is set as a reason for reissuance of the sterilization label 20 that an indicator has been forgotten to be housed in the packaging body 6 with the instrument set 8. In this preferred embodiment, in performing sterilization processing, an indicator is housed with the instrument set 8 in the packaging body 6. The indicator is configured such that a color thereof changes when sterilization is properly performed. The operator can check whether sterilization processing has been properly performed on the instrument set 8 by viewing the color of the indicator. For example, in a case where the indicator has been forgotten to be housed, in order to house the indicator, the packaging body 6 is torn. The torn packaging body 6 is discarded, and the instrument set 8 and the indicator are housed in a new packaging body 6. Thus, the sterilization label 20 is reissued to be attached to the new packaging body 6.

In this preferred embodiment, as illustrated in FIG. 8, the reason specifying area 121 of the reissuance reason registration screen DP20 is configured such that the operator can select one of the sterilization validity expiration reason 26, the package damage reason 27, the label damage reason 28, and the IC missing reason 29 included in the reissuance reason type 25. The operator can select one of the sterilization validity expiration reason 26, the package damage reason 27, the label damage reason 28, and the IC missing reason 29 by operating the operation device 55.

The confirmation button BT20 is a button used for confirming the reissuance reason type 25 of the sterilization label 20 and executing reissuance of the sterilization label 20. Herein, after selecting one of the reasons included as the reissuance reason type 25, the operator presses the confirmation button BT20 via the operation device 55. In the above-described manner, when the confirmation button BT20 is pressed by the operator, the process proceeds to Step S105 of FIG. 6 next.

In Step S105, the acquirer 65 of FIG. 4 acquires the reissuance reason type 25. Herein, the acquirer 65 acquires the reissuance reason type 25 specified in the reason specifying area 121 of the reissuance reason registration screen DP20. Specifically, the acquirer 65 generates the sterilization label information 130 (see FIG. 5) in which the target set ID 9 of the instrument set 8 that is a target to which the sterilization label 20 is reissued and the reissuance reason type 25 are associated with one another. The acquirer 65 causes the storage 61 of the memory 60a to store the generated sterilization label information 130. Herein, the acquirer 65 causes the storage 61 to store the generated sterilization label information 130 by adding the generated sterilization label information 130 to the sterilization label information list table TB30 (see FIG. 5).

The sterilization label information 130 generated by the acquirer 65 is, as illustrated in FIG. 5, information in which the sterilization ID 131, the set ID 132, the set name 133, the rack name 134, the user ID 135, the user name 136, the reissuance reason type 137, and the label issuance date 138 are associated with one another. When the confirmation button BT20 of the reissuance reason registration screen DP20 is pressed, the acquirer 65 automatically issues the sterilization ID 131. The acquirer 65 adds the target set ID 9 of the instrument set 8 that is a target to which the sterilization label 20 is reissued to the set ID 132 and adds the set name of the instrument set 8 assigned the target set ID 9 to the set name 133. The set name of the instrument set can be extracted, for example, from the above-described instrument set information.

The acquirer 65 adds the rack name displayed in the rack name area 106 of the label reissuing screen DP10 of FIG. 7 to the rack name 134. The acquirer 65 adds the user ID and the user name of the operator who issued the sterilization label 20 to the user ID 135 and the user name 136, respectively. In this preferred embodiment, when displaying the label reissuing screen DP10 on the display device 50, the operator inputs the user ID. The user ID input by the operator at this time is added to the user ID 135 of the sterilization label information 130 and the user name corresponding to the user ID input by the operator is added to the user name 136 of the sterilization label information 130.

In this preferred embodiment, the acquirer 65 adds the reissuance reason type 25 (herein, any one of the sterilization validity expiration reason 26, the package damage reason 27, the label damage reason 28, and the IC missing reason 29) specified by the operator in the reason specifying area 121 of the reissuance reason registration screen DP20 illustrated in FIG. 8 to the reissuance reason type 137 of the sterilization label information 130. Note that, herein, as described above, the sterilization label information 130 is generated not only when the sterilization label 20 is reissued but also when the sterilization label 20 is issued for the first time, and is added to the sterilization label information list table TB30. When the sterilization label 20 is issued for the first time, a null character is added to the reissuance reason type 137 of the sterilization label information 130.

The acquirer 65 adds a date of issuance of the sterilization label 20 to the label issuance date 138. In this preferred embodiment, a date on which the label issuing button BT10 of the label reissuing screen DP10 (see FIG. 7) was pressed is added as the date of issuance of the sterilization label 20 to the label issuance date 138. The sterilization label information 130 described above is generated and is added to the sterilization label information list table TB30, so that the reissuance reason type 25 is registered in the instrument management device 60.

After the reissuance reason type 25 is registered in the above-described manner, next, in Step S107 of FIG. 6, the label issuer 67 of FIG. 4 reissues the sterilization label 20. Herein, the label issuer 67 causes the label issuing machine 58 of FIG. 1 to print the sterilization identification mark 21 or the like on a label medium. At this time, the target sterilization ID 22 recorded in the sterilization identification mark 21 printed on the label medium is the sterilization ID 131 of the sterilization label information 130 (see FIG. 5) generated in Step S105. Note that Step S105 and Step S107 may be simultaneously executed, and Step S105 may be executed after Step S107. In the manner described above, the sterilization label 20 is reissued.

Figure 9:
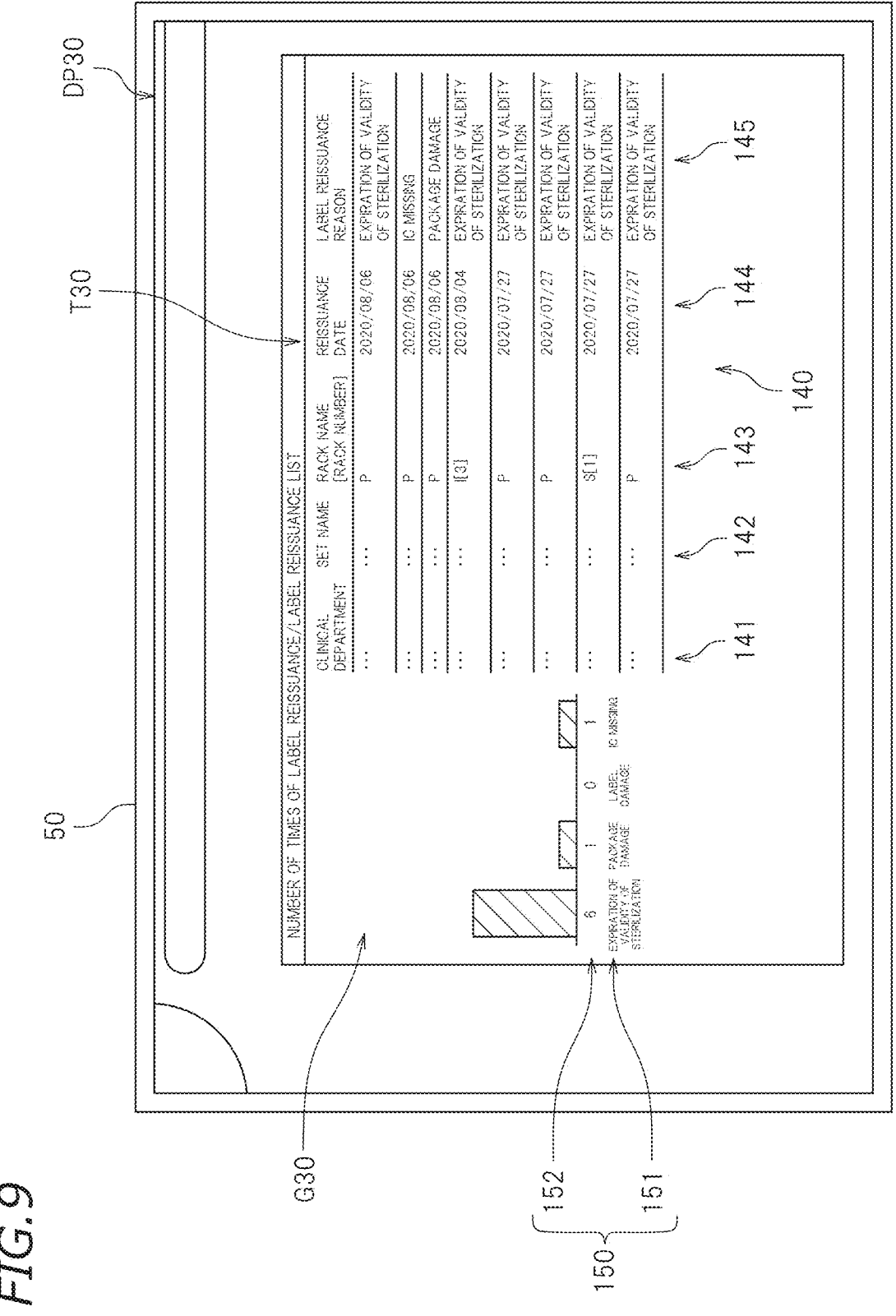
FIG. 9 is a view illustrating a reissuance reason tabulation screen.

In this preferred embodiment, the display section 63 can display the reissuance reason tabulation screen DP30 illustrated in FIG. 9 on the display device 50. Herein, in the reissuance reason tabulation screen DP30, a reissuance reason list table T30 and a number of times of reissuance graph G30 are arranged. Herein, the reason display section 73 of FIG. 4 displays the reissuance reason list table T30 on the display device 50 via the reissuance reason tabulation screen DP30. In the reissuance reason list table T30, information related to the target instrument set 8 that is a target to which the sterilization label 20 has been reissued is displayed. Herein, the reissuance reason list table T30 is a list table based on instrument and reissuance reason information 140.

The instrument and reissuance reason information 140 is information generated based on the sterilization label information 130 of the sterilization label information list table TB30 of FIG. 5. Specifically, the sterilization label information 130 in which the reissuance reason type 137 is indicated (in other words, not a null character but a reason is indicated) is extracted from the sterilization label information list table TB30, and the instrument and reissuance reason information 140 of the reissuance reason list table T30 is generated from the extracted sterilization label information 130.

The instrument and reissuance reason information 140 illustrated in FIG. 9 is information in which at least a set name 142 of the instrument set 8 assigned the target set ID 9 (see FIG. 3) and a reissuance reason type 145 are associated with one another. In this preferred embodiment, in the instrument and reissuance reason information 140, a clinical department 141, a set name 142, a rack name 143, a reissuance date 144, and a reissuance reason type 145 are associated with one another. The set name 133 associated with the reissuance reason type 137 indicating any one of the reasons 26 to 29 (see FIG. 8) in the sterilization label information 130 of FIG. 5 is added to the set name 142. A clinical department in which the instrument set 8 indicating the set name 133 is used is added to the clinical department 141. Although not illustrated, instrument and clinical department master information in which the set name or the set ID of the instrument set 8 and the clinical department are associated with one another is stored in advance in the storage 61. The clinical department associated with the set name 133 is extracted from the instrument and clinical department master information, and the extracted clinical department is added to the clinical department 141 of the instrument and reissuance reason information 140.

In the sterilization label information 130 of FIG. 5, the rack name 134 associated with the reissuance reason type 137 indicating any one of the reasons 26 to 29 is added to the rack name 143 of the instrument and reissuance reason information 140. In the sterilization label information 130, the label issuance date 138 associated with the reissuance reason type 137 indicating any one of the reasons 26 to 29 is added to the reissuance date 144. The reissuance reason type 137 of the sterilization label information 130 is added to the reissuance reason type 145 of the instrument and reissuance reason information 140. The reason display section 73 of FIG. 4 displays the instrument and reissuance reason information 140 generated in the above-described manner on the display device 50 via the reissuance reason list table T30.

In this preferred embodiment, the tabulation display section 75 of FIG. 4 displays the number of times of reissuance graph G30 on the display device 50. The number of times of reissuance graph G30 is a graph based on the sterilization label information 130 of the sterilization label information list table TB30 of FIG. 5 and is a graph corresponding to the instrument and reissuance reason information 140 of the reissuance reason list table T30 illustrated in FIG. 9.

The number of times of reissuance graph G30 is achieved by graphing a number of times of reissuance information 150. Herein, the number of times of reissuance information 150 is information in which a reissuance reason type 151 and a number of times of reissuance 152 are associated with one another.

The reissuance reason type 151 includes the sterilization validity expiration reason 26, the package damage reason 27, the label damage reason 28, and the IC missing reason 29. The number of times of reissuance 152 is calculated by the counter 71 of FIG. 4. Herein, the counter 71 counts, for each of reasons included as the reissuance reason type 151, the number of times of reissuance 152, that is, the number of times the sterilization label 20 has been reissued, for a reason of the reissuance reason type 151. In this preferred embodiment, the counter 71 extracts, from the sterilization label information 130 of FIG. 5, the sterilization label information 130 in which the reason is indicated in the reissuance reason type 137. Next, the counter 71 counts the number of times of reissuance for each of reasons included as the reissuance reason type 137, that is, for each of the sterilization validity expiration reason 26, the package damage reason 27, the label damage reason 28, and the IC missing reason 29.

Herein, the counter 71 counts, for example, the number of the sterilization label information 130, that is, the number of rows in the sterilization label information list table TB30, in which the reissuance reason type 137 is the sterilization validity expiration reason 26 to calculate the number of times of reissuance 152 for the sterilization validity expiration reason 26 included in the reissuance reason type 151. Similarly, the counter 71 counts the number of the sterilization label information 130 in which the reissuance reason type 137 is the package damage reason 27 to calculate the number of times of reissuance 152 for the package damage reason 27 included in the reissuance reason type 151. The counter 71 counts the number of the sterilization label information 130 in which the reissuance reason type 137 is the label damage reason 28 to calculate the number of times of reissuance 152 for the label damage reason 28 included in the reissuance reason type 151. The counter 71 counts the number of the sterilization label information 130 in which the reissuance reason type 137 is the IC missing reason 29 to calculate the number of times of reissuance 152 for the IC missing reason 29 included in the reissuance reason type 151.

The number of times of reissuance information 150 in which the number of times of reissuance 152 calculated by the counter 71 in the above-described manner and the reissuance reason type 151 are associated is generated. Based on the number of times of reissuance information 150, the tabulation display section 75 of FIG. 4 graphs the number of times of reissuance 152 for the sterilization validity expiration reason 26, the number of times of reissuance 152 for the package damage reason 27, the number of times of reissuance 152 for the label damage reason 28, and the number of times of reissuance 152 for the IC missing reason 29, generates the number of times of reissuance graph G30, and displays the number of times of reissuance graph G30 on the display device 50. Note that there is no particular limitation on a type of the number of times of reissuance graph G30 but, herein, the number of times of reissuance graph G30 is a bar graph for each of the reasons included as the reissuance reason type 151.

Figure 10:
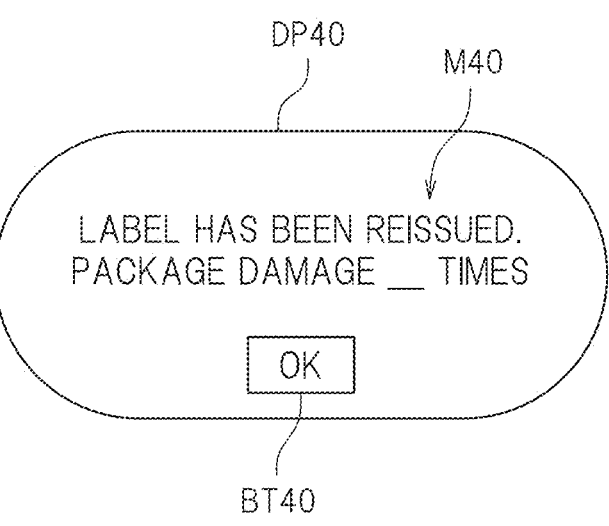
FIG. 10 is a view illustrating a warning screen.

Note that, in this preferred embodiment, in each of the processes 11 to 16 of the circulation cycle 10 of FIG. 2, in handing the instrument set 8, if the sterilization label 20 has been reissued in the past to the instrument set 8 that is a target to be handled, the display section 63 of FIG. 4 may display a warning screen DP40 illustrated in FIG. 10 on the display device 50. In this case, for example, in a case where not a null character but any one of the reasons 26 to 29 is indicated as the reissuance reason type 137 associated with the set ID 132 that matches the target set ID 9 of the instrument set 8 that is a target to be handled, the display section 63 displays the warning screen DP40.

On the warning screen DP40, for example, a warning message M40 and an OK button BT40 are arranged. The warning message M40 is a message indicating that the sterilization label 20 has been reissued before to the instrument set 8 that is handled. The operator can know that he or she handles the instrument set 8 to which the sterilization label 20 has been reissued in the past by viewing the warning message M40. Note that a reissuance reason type at a reissuance of the sterilization label 20 to the instrument set 8 that is a target to be handled, the number of times the sterilization label 20 has been reissued to the instrument set 8 that is a target to be handled, or the like may be displayed on the warning screen DP40. The operator presses the OK button BT40 via the operation device 55 to close the warning screen DP40.

As described above, in this preferred embodiment, as illustrated in FIG. 4, the instrument management device 60 includes the memory 60*a* and the at least one processor 60*b*. The at least one processor 60*b* is configured or programmed to execute display processing, acquisition processing, and counting processing. The display processing is executed by the display section 63 of FIG. 4. In the display processing, as in Step S103 of FIG. 6, in reissuing the sterilization label 20 that was issued when sterilization processing was performed on the instrument set 8 including one or more medical instruments 5, as illustrated in FIG. 8, the reissuance reason registration screen DP20 including the reason specifying area 121 via which the operator specifies the reissuance reason type 25 is displayed on the display device 50. The acquisition processing is executed by the acquirer 65 of FIG. 4. In the acquisition processing, as in Step S105 of FIG. 6, the reissuance reason type 25 specified in the reason specifying area 121 is acquired and is stored in the memory 60*a* (herein, the storage 61). The counting processing is executed by the counter 71 of FIG. 4. In the counting processing, for each of the reasons includes as the reissuance reason type 137 (see FIG. 5) stored in the memory 60*a* (herein, the storage 61), the number of times of reissuance 152 (see FIG. 9) that is the number of times the sterilization label 20 has been reissued for a reason of the reissuance reason type 137 is counted.

In this preferred embodiment, in reissuing the sterilization label 20, as illustrated in FIG. 8, the operator specifies the reissuance reason type 25 in the reason specifying area 121, so that for what reason the sterilization label 20 is reissued can be stored in the memory 60*a* (herein, the storage 61). For each of the reasons included as the reissuance reason type

137 of FIG. 5, the number of times of reissuance 152 (see FIG. 9) is counted. Accordingly, as illustrated in FIG. 9, the operator can know for which reason of the reissuance reason type 151 the sterilization label 20 has been reissued many times is by knowing the number of times of reissuance 152 for each of the reasons included as the reissuance reason type 151. Therefore, the operator can consider countermeasures for reducing the number of times of reissuance 152 for reissuance for a reason of the reissuance reason type 151 for which the sterilization label 20 has been reissued many times.

In this preferred embodiment, as illustrated in FIG. 8, the reissuance reason registration screen DP20 displayed in the display processing includes the confirmation button BT20 used for confirming the reissuance reason type 25 specified in the reason specifying area 121. In the acquisition processing executed by the acquirer 65 of FIG. 4, when the confirmation button BT20 is pressed, the reissuance reason type 25 specified in the reason specifying area 121 is acquired. Thus, even in a case where a wrong reissuance reason type 25 is specified in the reason specifying area 121, the reissuance reason type 25 specified in the reason specifying area 121 can be changed before the confirmation button BT20 is pressed.

In this preferred embodiment, in the acquisition processing executed by the acquirer 65 of FIG. 4, the sterilization label information 130 (see FIG. 5) in which the set ID 132 (see FIG. 5) to which the target set ID 9 assigned to the instrument set 8 that is a target to which the sterilization label 20 is reissued has been added and the reissuance reason type 137 (see FIG. 5) to which the reissuance reason type 25 specified in the reason specifying area 121 has been added are associated with one another is stored in the memory 60*a*. Thus, to what kind of instrument set 8 the sterilization label 20 has been reissued based on the what reissuance reason type 137 can be known. Accordingly, for each instrument set 8, countermeasures for reducing the number of times the sterilization label 20 is reissued can be considered.

In this preferred embodiment, the memory 60*a* stores the sterilization label information list table TB30 illustrated in FIG. 5. In the acquisition processing executed by the acquirer 65, the generated sterilization label information 130 is added to the sterilization label information list table TB30. Thus, the sterilization label information 130 is managed by a table of a database, and therefore, addition, deletion, and change of the sterilization label information 130 can be easily performed.

In this preferred embodiment, the at least one processor 60*b* is configured or programmed to execute reason display processing. The reason display processing is executed by the reason display section 73 of FIG. 4. In the reason display processing, the instrument and reissuance reason information 140 that is generated based on the sterilization label information 130 (see FIG. 5) stored in the memory 60*a* (herein, the storage 61) and in which, as illustrated in FIG. 9, the set name 142 of the instrument set 8 assigned the target set ID 9 (see FIG. 3) and the reissuance reason type 145 are associated with one another is displayed on the display device 50. Thus, the operator can easily visually know for which reason of the reissuance reason type 145 the sterilization label 20 has been reissued to what kind of instrument set 8 by viewing the instrument and reissuance reason information 140 displayed on the display device 50.

In this preferred embodiment, the at least one processor 60*b* is configured or programmed to execute tabulation display processing. The tabulation display processing is executed by the tabulation display section 75 of FIG. 4. In the tabulation display processing, as illustrated in FIG. 9, the number of times of reissuance information 150 in which the reissuance reason type 151 and the number of times of reissuance 152 counted in the counting processing executed by the counter 71 of FIG. 4 associated with one another is displayed on the display device 50. Thus, the operator can easily visually know for which reason of the reissuance reason type 151 the sterilization label 20 has been reissued many times by reviewing the number of times of reissuance information 150 displayed on the display device 50.

In this preferred embodiment, in the tabulation display processing executed by the tabulation display section 75 of FIG. 4, as illustrated in FIG. 9, the number of times of reissuance graph G30 achieved by graphing the number of times of reissuance information 150 is displayed on the display device 50. Thus, the operator can easily visually know for which reason of the reissuance reason type 151 the sterilization label 20 has been reissued many times by viewing the number of times of reissuance graph G30.

In this preferred embodiment, as illustrated in FIG. 8, as the reissuance reason type 25 that can be specified in the reason specifying area 121, at least the sterilization validity expiration reason 26, the package damage reason 27, the label damage reason 28, and IC missing reason 29 are included. For the sterilization validity expiration reason 26, the sterilization label 20 is reissued because a term of validity of sterilization processing performed on the instrument set 8 has expired. For the package damage reason 27, the sterilization label 20 is reissued because the packaging body 6 (see FIG. 3) in which the one or more medical instruments 5 forming the instrument set 8 are housed is damaged. For the label damage reason 28, the sterilization label 20 is reissued because the sterilization label 20 is damaged. For the IC missing reason 29, the sterilization label 20 is reissued because the indicator indicating that sterilization processing has been performed on the instrument set 8 has been forgotten to be housed in the packaging body 6. It can be considered that, as a reason why the sterilization label 20 is reissued, the sterilization validity expiration reason 26, the package damage reason 27, the label damage reason 28, and the IC missing reason 29 highly frequently arise. Accordingly, by configuring such that, as the reissuance reason type 25, the sterilization validity expiration reason 26, the package damage reason 27, the label damage reason 28, and the IC missing reason 29 can be specified in the reason specifying area 121, the operator can easily specify the reissuance reason type 25.

In this preferred embodiment, as illustrated in FIG. 1, the instrument management system 100 includes the instrument management device 60, the display device 50, the operation device 55, and the label issuing machine 58 that issues the sterilization label 20. The at least one processor 60b of the instrument management device 60 is configured or programmed to execute label issuance processing. The label issuance processing is executed by the label issuer 67 of FIG. 4. In the label issuance processing, as in Step S107 of FIG. 6, when the reissuance reason type 25 (see FIG. 8) specified in the reason specifying area 121 is acquired in the acquisition processing executed by the acquirer 65 of FIG. 4, the label issuing machine 58 is caused to issue the sterilization label 20. Thus, the sterilization label 20 can be reissued in a timing in which the reissuance reason type 25 specified by the operator is acquired.

In this preferred embodiment, as illustrated in FIG. 3, the sterilization identification mark 21 in which the target sterilization ID 22 indicating that sterilization processing has been performed on the instrument set 8 that is a target to which the sterilization label 20 is issued is recorded is assigned to the sterilization label 20. The label issuing machine 58 of FIG. 1 is a printer. In the label issuance processing realized by the label issuer 67 of FIG. 4, by causing the label issuing machine 58 to print the sterilization identification mark 21 on a predetermined label medium, the sterilization label 20 can be easily issued.

Note that, in this preferred embodiment, an instrument management method for the medical instrument 5 can be realized by the instrument management device 60 for the medical instrument 5. The instrument management method for medical instrument 5 according to this preferred embodiment includes a display step, an acquisition step, a label issuance step, a counting step, a reason display step, and a tabulation display step. The display step, the acquisition step, the label issuance step, the counting step, the reason display step, and the tabulation display step are realized by the display section 63, the acquirer 65, the label issuer 67, the counter 71, the reason display section 73, and the tabulation display section 75 of the instrument management device 60, respectively.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:

1. An instrument management device for a medical instrument, the instrument management device comprising:
 a memory; and
 at least one processor to execute a program stored in the memory to perform:
   display processing to display, in reissuing a sterilization label that is issued when sterilization processing is performed on an instrument set including one or more medical instruments, a reissuance reason registration screen including a reason specifying area via which an operator specifies a type of reissuance reason that is a reason for reissuing the sterilization label on a display device;
   acquisition processing to acquire the type of reissuance reason specified in the reason specifying area and storing the type of reissuance reason in the memory; and
   counting processing to count, for each of the types of reissuance reason stored in the memory, a number of times of reissuance that is a number of times the sterilization label has been reissued for a reason of the type of reissuance reason, wherein
   in the acquisition processing, a sterilization identification mark of the sterilization label that has been issued to the instrument set is read by a reading device to acquire a target set ID, and
   in the acquisition processing, sterilization label information in which the target set ID assigned to an instrument set that is a target to which the sterilization label is reissued and the type of reissuance reason specified in the reason specifying area are associated with one another is stored in the memory.
2. The instrument management device for a medical instrument according to claim 1, wherein
   the reissuance reason registration screen displayed in the display processing includes a confirmation button used to confirm the type of reissuance reason specified in the reason specifying area; and in the acquisition processing, the type of reissuance reason specified in the reason specifying area when the confirmation button is pressed is acquired.

3. The instrument management device for a medical instrument according to claim 1, wherein the memory stores a sterilization label information table; and in the acquisition processing, the sterilization label information is added to the sterilization label information table.

4. The instrument management device for a medical instrument according to claim 1, wherein the instrument management device is configured or programmed to execute reason display processing to display instrument and reissuance reason information that is generated based on the sterilization label information stored in the memory and in which a set name of the instrument set assigned the target set ID and the type of reissuance reason are associated with one another on the display device.

5. The instrument management device for a medical instrument according to claim 1, wherein the instrument management device is configured or programmed to execute tabulation display processing to display a number of times of reissuance information in which the type of reissuance reason and the number of times of reissuance counted in the counting processing are associated with one another on the display device.

6. The instrument management device for a medical instrument according to claim 5, wherein, in the tabulation display processing, a number of times of reissuance graph achieved by graphing the number of times of reissuance information is displayed on the display device.

7. The instrument management device for a medical instrument according to claim 1, wherein, the type of reissuance reason that can be specified via the reason specifying area includes at least:

a sterilization validity expiration reason for which the sterilization label is reissued because a term of validity of sterilization processing performed on the instrument set has expired;

a package damage reason for which the sterilization label is reissued because a packaging body in which the one or more medical instruments of the instrument set are housed is damaged;

a label damage reason for which the sterilization label is reissued because the sterilization label is damaged; and an IC missing reason for which the sterilization label is reissued because an indicator indicating that sterilization processing has been performed on the instrument set has been forgotten to be housed in the packaging body are included.

8. An instrument management system comprising:

the instrument management device for a medical instrument according to claim 1;

a display device; and an operation device.

9. The instrument management system according to claim 8, further comprising:

a label issuing machine that issues the sterilization label; wherein the instrument management device is configured or programmed to execute, when the type of reissuance reason specified in the reason specifying area is acquired in the acquisition processing, label issuance processing of causing the label issuing machine to issue the sterilization label.

10. The instrument management system according to claim 9, wherein the sterilization identification mark in which a target sterilization ID indicating that sterilization processing has been performed on the instrument set that is a target to which the sterilization label is issued is recorded is assigned to the sterilization label;

the label issuing machine includes a printer; and in the label issuance processing, by causing the label issuing machine to print the sterilization identification mark on a predetermined label medium, the sterilization label is issued.

11. An instrument management method for a medical instrument, the instrument management method comprising:

displaying, in reissuing a sterilization label that is issued when sterilization processing is performed on an instrument set including one or more medical instruments, a reissuance reason registration screen including a reason specifying area via which an operator specifies a type of reissuance reason that is a reason for reissuing the sterilization label on a display device;

acquiring the type of reissuance reason specified in the reason specifying area and storing the type of reissuance reason in the memory; and counting, for each of the types of reissuance reasons stored in the memory, a number of times of reissuance that is a number of times the sterilization label has been reissued for a reason of the type of reissuance reason, wherein in the acquiring, a sterilization identification mark of the sterilization label that has been issued to the instrument set is read by a reading device to acquire a target set ID, and in the acquiring, sterilization label information in which the target set ID assigned to an instrument set that is a target to which the sterilization label is reissued and the type of reissuance reason specified in the reason specifying area are associated with one another is stored in the memory.

12. The instrument management method for a medical instrument according to claim 11, further comprising:

displaying instrument and reissuance reason information that is generated based on the sterilization label information stored in the memory and in which a set name of the instrument set assigned the target set ID and the type of reissuance reason are associated with one another on the display device.

13. The instrument management method for a medical instrument according to claim 11, further comprising:

displaying number of times of reissuance information in which the type of reissuance reason and the number of times of reissuance counted in the counting are associated with one another on the display device.

* * * * *